(12) United States Patent
Tinger et al.

(10) Patent No.: US 10,196,329 B2
(45) Date of Patent: Feb. 5, 2019

(54) PROCESS FOR MAKING PARA-XYLENE

(71) Applicant: ExxonMobil Chemical Patents Inc., Baytown, TX (US)

(72) Inventors: Robert G. Tinger, Friendswood, TX (US); Gary D. Mohr, Sunset, SC (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/518,882

(22) PCT Filed: Oct. 16, 2015

(86) PCT No.: PCT/US2015/055904
§ 371 (c)(1),
(2) Date: Apr. 13, 2017

(87) PCT Pub. No.: WO2016/081110
PCT Pub. Date: May 26, 2016

(65) Prior Publication Data
US 2017/0240487 A1 Aug. 24, 2017

Related U.S. Application Data

(60) Provisional application No. 62/082,885, filed on Nov. 21, 2014.

(51) Int. Cl.
*C07C 2/66* (2006.01)
*B01D 3/00* (2006.01)
(Continued)

(52) U.S. Cl.
CPC ............ *C07C 2/66* (2013.01); *B01D 3/009* (2013.01); *C07C 2/864* (2013.01); *C07C 2/865* (2013.01);
(Continued)

(58) Field of Classification Search
CPC ...................................................... C07C 6/04
See application file for complete search history.

(56) References Cited

U.S. PATENT DOCUMENTS 3,067,270 A   12/1962  Weedman
3,177,255 A   4/1965   Ehrhart et al.
(Continued)

FOREIGN PATENT DOCUMENTS

CA   1242309 A1 * 9/1988 ............... B01D 3/00
CN   102190553      3/2014
(Continued)

OTHER PUBLICATIONS

Kiss, Applications of Dividing Wall Columns, Advanced Distillation Technologies: Design, Control, and Applications. 2013, pp. 187, 195, and 197. (Year: 2013).*
(Continued)

*Primary Examiner* — Philip Y Louie
*Assistant Examiner* — Alyssa L Cepluch

(57) ABSTRACT

Disclosed is a process for making para-xylene from toluene and/or benzene comprising (i) converting toluene and/or benzene to a first product mixture comprising mixed xylenes, (ii) obtaining a xylene mixture from the first product mixture, (iii) separating para-xylene from the xylene mixture, and (iv) transalkylating meta-xylene and/or ortho-xylene with toluene and/or benzene.

21 Claims, 3 Drawing Sheets

(51) Int. Cl.
*C07C 7/04* (2006.01)
*C07C 6/04* (2006.01)
*C07C 7/14* (2006.01)
*C07C 2/86* (2006.01)
*C07C 6/12* (2006.01)
*C07C 7/13* (2006.01)

(52) U.S. Cl.
CPC ............... *C07C 6/04* (2013.01); *C07C 6/123* (2013.01); *C07C 6/126* (2013.01); *C07C 7/04* (2013.01); *C07C 7/13* (2013.01); *C07C 7/14* (2013.01); *C07C 2529/06* (2013.01); *Y02P 20/127* (2015.11)

(56) References Cited

U.S. PATENT DOCUMENTS

| | | |
|---|---|---|
| 3,467,724 A | 9/1969 | Laurich |
| 3,702,886 A | 11/1972 | Argauer et al. |
| 3,709,979 A | 1/1973 | Chu |
| 3,832,449 A | 8/1974 | Rosinski et al. |
| 3,965,207 A | 6/1976 | Weinstein |
| 4,016,218 A | 4/1977 | Haag et al. |
| 4,016,245 A | 4/1977 | Plank et al. |
| 4,076,842 A | 2/1978 | Plank et al. |
| 4,356,338 A | 10/1982 | Young |
| 4,375,573 A | 3/1983 | Young |
| 4,582,815 A | 4/1986 | Bowes |
| 4,670,616 A | 6/1987 | De Simone et al. |
| 5,053,374 A | 10/1991 | Absil et al. |
| 5,110,776 A | 5/1992 | Chitnis et al. |
| 5,182,242 A | 1/1993 | Marler |
| 5,231,064 A | 7/1993 | Absil et al. |
| 5,284,992 A | 2/1994 | Hotier et al. |
| 5,348,643 A | 9/1994 | Absil et al. |
| 5,365,003 A | 11/1994 | Chang et al. |
| 6,111,157 A * | 8/2000 | Hendriksen ............... B01J 29/80 502/67 |
| 6,689,929 B2 | 2/2004 | Williams et al. |
| 7,176,339 B2 | 2/2007 | Iaccino et al. |
| 7,563,358 B2 | 7/2009 | Stavens et al. |
| 7,629,498 B2 | 12/2009 | Brown et al. |
| 8,344,197 B2 | 1/2013 | Lattner et al. |
| 8,563,795 B2 * | 10/2013 | Negiz ...................... C07C 2/76 585/446 |
| 2003/0130549 A1 | 7/2003 | Xie et al. |
| 2012/0149958 A1 * | 6/2012 | Ellrich .................... C07C 2/864 585/321 |
| 2013/0144097 A1 | 6/2013 | Bender et al. |
| 2013/0267746 A1 * | 10/2013 | Ding ........................ C07C 6/06 585/319 |

FOREIGN PATENT DOCUMENTS

| | | | |
|---|---|---|---|
| EP | 0 276 524 | 8/1988 | |
| WO | 97/45387 | 12/1997 | |
| WO | WO-2012145233 A2 * | 10/2012 | ............ C07C 6/126 |
| WO | 2013/009399 | 1/2013 | |
| WO | 2013/095767 | 6/2013 | |
| WO | 2013/134038 | 9/2013 | |
| WO | 2013/169465 | 11/2013 | |
| WO | 2014/058550 | 4/2014 | |

OTHER PUBLICATIONS

Crank, *The Mathematics of Diffusion*, Second Edition, Clarendon Press, Oxford, 1975.

* cited by examiner

PROCESS FOR MAKING PARA-XYLENE

CROSS REFERENCE TO RELATED APPLICATIONS

This application is a U.S. National Phase application of PCT/US2015/055904, filed Oct. 16, 2015 which claims priority to and the benefit of U.S. Provisional Application No. 62/082,885, filed Nov. 21, 2014, both of which are incorporated herein by reference in their entirety for all purposes.

TECHNICAL FIELD

This invention relates to a process for making para-xylene. In particular, the present invention relates to a process for making para-xylene from feeds containing toluene and/or benzene.

BACKGROUND

Xylene isomers find wide and varied application. They are especially valuable as intermediates in chemical processes. By way of example, para-xylene is a feedstock for terephthalic acid, which finds use in the manufacture of polyester fibers and films, meta-xylene is used in the manufacture of dyes, and ortho-xylene is used as a feedstock for phthalic anhydride, which finds use in the manufacture of plasticizers. Para-xylene is currently the most valuable of the xylene isomers and, although research related to obtaining (e.g., producing or purifying) para-xylene is voluminous, there is still intensive research in the area.

There are many possible feeds currently used to obtain para-xylene. The majority of para-xylene produced today comes from catalytic reforming, which involves dehydrogenation and dehydrocyclization of naphtha feedstocks. The effluent of the reforming process, known as reformate, is rich in aromatics, particularly benzene, toluene, and mixed xylenes (BTX), and is used as feedstock to aromatics plants. Processes exist to increase the yield of para-xylene over the equilibrium mixture in the reformate, including selective toluene disproportionation and selective methylation of benzene and/or toluene with methanol.

Recently, significant research has focused on finding alternative sources and methods for producing BTX and particularly para-xylene. For example, although steam cracking, or pyrolysis, is the preferred method of producing light olefins (ethylene, propylene, and butenes) from heavier hydrocarbon feedstocks, the process also generates a by-product termed pyrolysis gasoline, steam cracked naphtha (SCN) or pygas. Pygas is a complex mixture of C6 to C10+ hydrocarbons that is rich in aromatics, particularly benzene and toluene, but also contains C8, C9, and C10+ aromatics. Similarly, catalytic cracking, particularly fluid catalytic cracking (FCC), in addition to producing fuels and light olefins, generates a C6 to C10+ aromatic rich stream which is similar to pygas and is generally known as cat naphtha. These processes also produce C4 and C5 olefinic streams (containing di-olefins and acetylenes) which have some utility but tend to be of lower value than aromatic products and lighter olefins (ethylene and propylene). There is, therefore, significant interest in developing methods of upgrading alternate feed sources, such as pygas and cat naphtha, to increase the yield of ethylene, propylene, BTX; and preferably para-xylene and propylene. There are some processes proposed to upgrade these streams to produce BTX but they consume expensive hydrogen and co-produce lower value light saturates rather than higher value light olefins.

U.S. Pat. No. 7,176,339 discloses a process for producing xylenes from reformate, which process comprises: (a) providing a reformate containing hydrogen, C1 to C5 hydrocarbons, C6 to C7 hydrocarbons comprising benzene, toluene or mixtures thereof, and C8+ hydrocarbons; (b) removing at least a portion of said hydrogen from said reformate to produce a product containing C6 to C7 hydrocarbons comprising benzene, toluene, or mixtures thereof, and C8+ hydrocarbons; and (c) methylating at least a portion of the benzene, toluene, or mixtures thereof present in said product with a methylating agent under vapor phase conditions and in the presence of a catalyst effective for the methylation to produce a resulting product having a higher para-xylene content than the reformate. The catalyst comprises a zeolite-bound-zeolite catalyst and/or a selectivated zeolite and the zeolite comprises ZSM-5. A similar process is disclosed in U.S. Pat. No. 7,629,498.

U.S. Pat. No. 7,563,358 discloses process for producing BTX-enriched product from a hydrocarbon feed comprising: (a) C6+ non-aromatic cyclic hydrocarbons; (b) C8+ single-ring aromatic hydrocarbons having at least one alkyl group containing two or more carbon atoms; and (c) C9+A single-ring aromatic hydrocarbons having at least three methyl groups. According to the process, the feed is contacted, in the presence of hydrogen, with a catalyst comprising at least one Group VIII metal and a large or intermediate pore molecular sieve having an alpha value, before incorporation of the Group VIII metal, from about 2 to less than 100 under conditions sufficient for (i) forming aromatic hydrocarbons from C6+ non-aromatic cyclic hydrocarbons; (ii) dealkylating C8+ single-ring aromatic hydrocarbons having at least one alkyl group containing two or more carbon atoms; (iii) transalkylating C9+ single-ring aromatic hydrocarbons having at least three methyl groups; and (iv) disproportionating toluene, to produce a product containing an increased amount of BTX compared to the feed. A preferred hydrocarbon feed is steam cracked naphtha.

Given the higher value of xylenes, especially para-xylene, than toluene and benzene, there is a desire to convert a portion of the toluene and benzene produced in the above petrochemical processes to xylenes, especially para-xylene. The present invention provides an effective process for doing so.

SUMMARY

It has now been found that by first converting toluene and/or benzene to xylenes by methylation and/or disproportionation, followed by separation to obtain a para-xylene product and a meta-xylene and ortho-xylene mixture, and subsequently converting a portion of the meta-xylene and ortho-xylene mixture to para-xylene by transalkylation with benzene and/or toluene, one can produce para-xylene with a high yield and high energy efficiency. The transalkylation step allows for a higher xylene concentration in the feed supplied to the separation step, higher separation efficiency, and hence the use of a smaller separation device, and lower capital and operation costs thereof.

Accordingly, the present invention provides a process for making para-xylene, the process comprising: (A) feeding a first feed comprising toluene and/or benzene and optionally a second feed comprising a methylation agent to a first reactor; (B) conducting reactions in the first reactor to produce a first product mixture comprising toluene and mixed xylenes, and optionally benzene; (C) separating the first product mixture in a first separation device to obtain a first toluene-rich stream and a first xylene-rich stream; (D) separating the first xylene-rich stream in a second separation device to obtain a para-xylene-rich product stream, and a meta-xylene-rich stream; (E) feeding a third feed comprising benzene and optionally toluene and at least a portion of the meta-xylene-rich stream to a second reactor; and (F) conducting transalkylation reactions in the second reactor to obtain a second reaction product mixture comprising benzene, toluene, and mixed xylenes.

DETAILED DESCRIPTION

Figure 1:
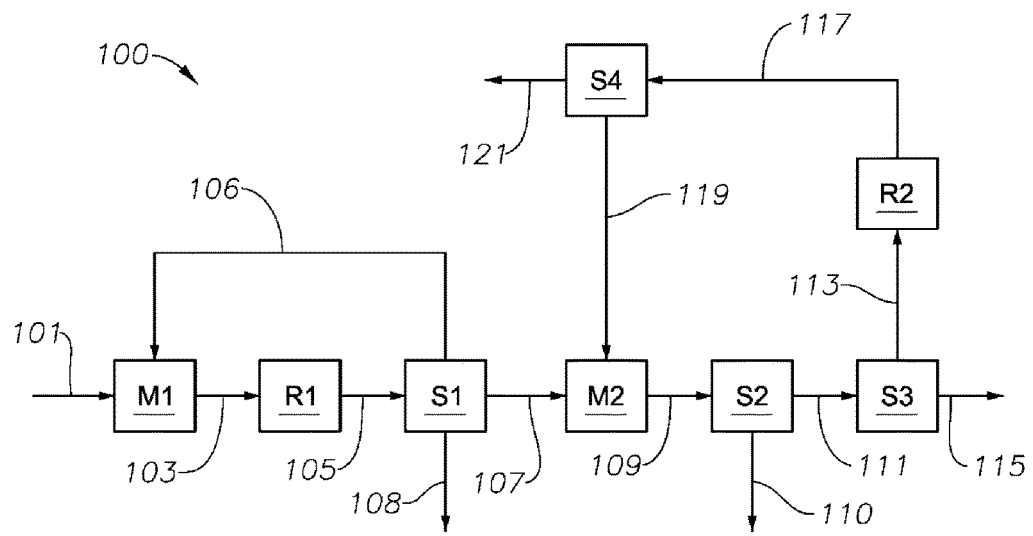
FIG. 1 is a schematic diagram showing a comparative process for making para-xylene from benzene, toluene and methanol that is not conducted according to the present invention.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents comprising elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a distillation column" include embodiments where one, two or more distillation columns are used, unless specified to the contrary or the context clearly indicates that only one distillation column is used. Likewise, "a C9+A component" should be interpreted to include one, two or more C9+A components unless specified or indicated by the context to mean only one specific C9+A component.

As used herein, the generic term "xylene," either in singular or plural form, shall collectively mean any mixture of two or three of para-xylene, meta-xylene, and ortho-xylene at any proportion thereof. The term "mixed xylenes" means a combination of all three isomers of xylene.

As used herein, the term "rich" when used in phrases such as "X-rich" or "rich in X" means, with respect to an outgoing stream obtained from a device, that the stream comprises material X at a concentration higher than in the feed material fed to the same device from which the stream is derived.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. Thus, e.g., the concentrations of the various components of the first feed are expressed based on the total weight of the first feed. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

Benzene and/or Toluene Methylation

In one aspect, the reactions conducted in the first reactor in the process of the present invention can be entirely, primarily or partly an alkylation reaction between an aromatic compound and an alkylation agent.

Processes have been proposed for the production of xylenes by methylation of toluene and/or benzene using a zeolite catalyst. For instance, U.S. Pat. No. 3,965,207 discloses methylation of toluene using a zeolite catalyst such as a ZSM-5. U.S. Pat. No. 4,670,616 discloses production of xylenes by methylation of toluene using a borosilicate molecular sieve which is bound by a binder such as alumina, silica, or alumina-silica. WO2013/009399A1; WO1997/045387A1; and U.S. Pat. No. 8,344,197 describe various other alkylation processes for producing xylenes from benzene and/or toluene. The disclosures in all these references are incorporated herein by reference in their entirety.

The feed materials supplied to the alkylation step of a process of the present invention comprises an aromatic feed (i.e., contained in the first feed) and an alkylation agent (i.e., contained in the second feed). The first feed in general comprises toluene and/or benzene. Preferably, the first feed contains at least x wt % of benzene, toluene or a mixture thereof, where x can be 90, 91, 92, 93, 94, 95, 96, 97, 98, 99, or 100. An aromatic first feed containing at least y wt % toluene is particularly desirable, where y can be 90, 91, 92, 93, 94, 95, 96, 97, 98, 99, or even 100.

The alkylation agent in the second feed supplied to the alkylation step preferably comprises a methylation agent such as methanol, dimethyl ether, and mixtures thereof. The alkylation agent desirably comprises at least z wt % of methanol and/or dimethyl ether, where z can be 90, 91, 92, 93, 94, 95, 96, 97, 98, 99, or even 100. Preferably, the alkylation agent comprises at least a wt % of methanol, where a can be 90, 91, 92, 93, 94, 95, 96, 97, 98, 99, or even 100.

The aromatic first feed and the alkylation agent contained in the second feed may be mixed together before being supplied into the alkylation step in the first reactor. Alternatively or additionally, a portion of the aromatic first feed and/or alkylation agent second feed may be fed into the first reactor separately via separate feeding channels. Once delivered into the first reactor, the aromatic feed and the alkylation agent mix with each other, contact each other in the presence of an alkylation catalyst under suitable alkylation reaction conditions to yield a mixture of xylenes.

Typically the alkylation catalyst employed in the alkylation step comprises a solid acid component capable of promoting the alkylation of an aromatic ring. The solid acid preferably comprises a molecular sieve of the following framework types: MAZ, MEI, FAU, EMT, MFI, MEL, MTW, EUO, MTT, HEU, FER, TON, CHA, ERI, KFI, LEV, and LTA. The alkylation catalyst can comprise a porous crystalline material. The catalyst may have a Diffusion Parameter for 2,2-dimethylbutane of about 0.1 to 15 second$^{-1}$ when measured at a temperature of 120° C. and a 2,2-dimethylbutane pressure of 60 torr (8 kPa).

As used herein, the Diffusion Parameter of a particular porous crystalline material is defined as $D/r^2 \times 10^6$, wherein D is the diffusion coefficient (cm$^2$/second) and r is the crystal radius (cm). The required diffusion parameters can be derived from sorption measurements provided the assumption is made that the plane sheet model describes the diffusion process. Thus, for a given sorbate loading Q, the value Q/Q', where Q' is the equilibrium sorbate loading, is mathematically related to $(Dt/r^2)^{1/2}$ where t is the time (second) required to reach the sorbate loading Q. Graphical solutions for the plane sheet model are given by J. Crank in "The Mathematics of Diffusion", Oxford University Press, Ely House, London, 1967.

The porous crystalline material preferably comprises a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1 to 12, as measured on the zeolite alone without the introduction of oxide modifiers and prior to any steaming to adjust the diffusivity of the catalyst.

In addition to the medium-pore size aluminosilicate zeolites, other medium pore acidic metallosilicates, such as silicoaluminophosphates (SAPOs), can be used in the alkylation step of the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof are taught by U.S. Pat. No. 4,375,573. The entire disclosures of these U.S. patents are incorporated herein by reference.

The medium pore zeolites described above are preferred for the present process since the size and shape of their pores favor the production of p-xylene over the other xylene isomers. However, conventional forms of these zeolites have Diffusion Parameter values in excess of the 0.1-15 second$^{-1}$ range preferred for the present process. Nevertheless, the required diffusivity can be achieved by severely steaming the zeolite so as to effect a controlled reduction in the micropore volume of the catalyst to not less than 50%, and preferably 50% to 90%, of that of the unsteamed catalyst. Reduction in micropore volume is derived by measuring the n-hexane adsorption capacity of the zeolite, before and after steaming, at 90° C. and 75 torr n-hexane pressure.

Steaming of the porous crystalline material is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups 2, 3, 5, 13, 14, 15, and 16. Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be from about 0.05 wt % to about 20 wt %, and preferably is from about 0.1 wt % to about 10 wt %, based on the weight of the final catalyst.

Where the modifier includes phosphorus, incorporation of modifier in the catalyst of the invention is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time form about 15 minutes to about 20 hours. The concentration of the phosphorus in the contact mixture may be from about 0.01 to about 30 wt %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3 to 5 hours.

The porous crystalline material employed in the present process may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

The relative proportions of porous crystalline material and inorganic oxide matrix can vary widely. The content of the porous crystalline material can range from about 1 wt % to about 90% by weight, and when the composite is prepared in the form of beads, preferably from about 2 wt % to about 80 wt %, of the composite.

In one embodiment, the binder material comprises silica or a kaolin clay. Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The present process can be conducted with the catalyst disposed in one or more fixed, moving or fluidized beds. Preferably, however, the catalyst particles are disposed in one or more fluidized beds. Each of the methanol and aromatic feeds can be injected into the fluidized catalyst in a single-stage. However, in a preferred embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Alternatively, the catalyst can be disposed in a plurality of vertically spaced fluidized catalyst beds, with the aromatic feed being injected into a lower portion of the first fluidized bed and part of the methanol being injected into an intermediate portion of the first bed and part of the methanol being injected into or between adjacent downstream catalyst beds.

Irrespective of the disposition of the catalyst, as the alkylation reaction proceeds the catalyst gradually deactivates as a result of build-up of carbonaceous material, generally referred to as "coke" on the catalyst. Thus, a portion of the catalyst in each alkylation reactor is generally withdrawn, either on a continuous or a periodic basis, and fed to a separate regenerator. In the regenerator, the catalyst, again preferably in the form of a fluidized bed, is contacted with an oxygen-containing gas, such as air, at a temperature from about 400° C. to about 700° C. so as to burn off the coke and regenerate the catalyst. The regenerated catalyst is then continuously or periodically returned to the alkylation reactor.

Generally, the conditions employed in the present alkylation process include a temperature from about 400° C. to about 800° C., such as from about 550° C. to about 650° C.; absolute internal total pressure from about 100 kPa to about 10,000 kPa, such as from about 100 kPa to 300 kPa; a molar ratio of aromatic to methanol in the reactor charge of at least about 0.2, and preferably from about 2 to about 20; and a weight hourly space velocity ("WHSV") for total hydrocarbon feed to the reactor(s) of about 0.2 to about 1000, preferably about 0.5 to about 500 for the aromatic reactant, and about 0.01 to about 100 for the methanol reagent, based on total catalyst in the reactor(s).

More specifically, the conditions in the alkylation process are controlled so as to maximize the selectivity of the reaction to the desired para-xylene product. In general, this is achieved by maintaining the reaction temperature at a relatively high value (about 590° C.) and operating with an excess of the aromatic reagent (a molar ratio of aromatic to methanol in the reactor charge of at least 2). Normally, the alkylation conditions are substantially adiabatic, that is heat is not actively added to or removed from the alkylation reactor system. Thus, all the heat required to maintain the reaction temperature at the desired value is provided by a combination of the heat initially supplied to the methanol and aromatic feeds and the exothermic heat generated in the reaction. In particular, the temperature control in the present process involves initially preheating the methanol and aromatic feeds to first and second predetermined temperatures, respectively, at or near the maximum values consistent with avoiding feed decomposition in the preheaters. In the case of the methanol feed, this involves preheating the feed to a first temperature from about 150° C. to about 300° C., such as about 220° C., whereas in the case of the aromatic feed the second temperature is from about 300° C. to about 700° C., such as about 550° C.

In addition, temperature control is effected by measuring the temperature in the alkylation reactor and comparing the measured temperature with a predetermined optimal temperature in the reactor (usually about 590° C.). The molar ratio of methanol to aromatic feedstock supplied to the reactor is then used to reduce any difference between the measured and predetermined optimal temperatures in the reactor, generally to a delta value that is less than 10° C., typically less than 5° C. Thus, since the conversion of methanol in the process, whether by alkylation or the production of light gases, is exothermic, any increase in the methanol to aromatic molar ratio will increase the supply of heat to the reaction and hence raise the reaction temperature. Alternatively, since conversion of methanol is the rate limiting step, any decrease in the methanol to aromatic molar ratio will decrease the supply of heat to the reaction and hence lower the reaction temperature. Controlling the reaction temperature in this manner enables that, for a given desired reaction temperature and maximum value of the feed preheating temperatures, the lowest possible methanol to aromatic molar ratio will be employed. This maintains the methanol concentration in the reactor at its lowest possible value, resulting in the highest possible selectivity to the desired xylene product.

For an adiabatic system, if the reactor is perfectly mixed, the temperature will be uniform throughout the reactor and all reactions will proceed at a single reaction temperature. Thus, in effecting temperature control, it is unimportant where the temperature in the reactor is measured. On the other hand, if the reactor is not perfectly mixed, or is plug flow, there will be a temperature profile across the reactor, with the highest temperature being at the reactor outlet. In this case, the reactor temperature is preferably measured at or near the point where the reaction effluent exits the reactor.

In one embodiment of the present process, the degree of conversion of methanol is also controlled so as to remain substantially constant. This can be achieved without disturbing the reaction temperature control by adjusting the amount of catalyst in the reactor, the catalyst activity or both. Adjustment of catalyst amount and activity are easiest to effect in a fluid bed system as described above. Thus, for example, the catalyst amount can be adjusted by adding or removing catalyst from the reactor, or by shifting the amount of catalyst in the reactor versus that in the regenerator, whereas the catalyst activity can be adjusted by changing either or both of the catalyst regeneration rate and the make-up rate of fresh catalyst.

Toluene Disproportionation

In another aspect, the reactions conducted in the first reactor in the process of the present invention can be entirely, primarily or partly toluene disproportionation. The first feed fed to the first reactor in this scenario therefore desirably comprises b wt % toluene, where b can be, e.g., 90, 91, 92, 93, 94, 95, 96, 97, 98, 99, or even 99.

Toluene disproportionation processes and/or catalysts are described in, e.g., U.S. Pat. Nos. 4,097,543; 4,851,604; 4,962,257; 5,030,787; 5,367,099; and 6,774,273, the disclosures of which are incorporated herein by reference in their entirety.

Toluene disproportionation catalysts can preferably comprise a molecular sieve of the following framework types: MAZ, MEI, FAU, EMT, MFI, MEL, MTW, EUO, MTT, HEU, FER, TON, CHA, ERI, KFI, LEV, and LTA. Examples of suitable zeolite molecular sieves include large pore zeolites, medium pore zeolites, and small pore zeolites. A large pore zeolite generally has a pore size of >7 Å and includes zeolite types such as MAZ, MEI, FAU, and EMT. Examples of large pore zeolites include zeolite L, zeolite Y, zeolite X, offretite, omega, Beta, mordenite, ZSM-3, ZSM-4, ZSM-18, and ZSM-20. A medium pore size catalyst generally has a pore size <7 Å, preferably from about 5 Å to about 6.8 Å; and generally the pore apertures consist of about 10 to 12, preferably about 10, membered ring structures and can include MFI, MEL, MTW, EUO, MTT, HEU, FER, and TON. Examples of medium pore zeolite include ZSM-34, ZSM-38, and ZSM-48. A small pore size zeolite has a pore size from about 3 Å to about 5.0 Å. Generally, the pore apertures of the structure consist of from about 8 to 10, preferably about 8, membered ring structures and include CHA, ERI, KFI, LEV, and LTA. Examples of small pore zeolite include ZK-4, ZK-5, zeolite A, zeolite T, gmelinite, clinoptilolite, chabasite and erionite. The zeolites can also comprise gallosilicates and titanosilicates.

Toluene disproportionation can be conducted substantially in vapor phase, where toluene contacts the catalyst under disproportionation conditions to yield a product mixture which comprises a mixture of benzene, unreacted (unconverted) toluene and mixed xylenes. Preferably, the catalyst can be first selectivated prior to use in the disproportionation process to enhance conversion of toluene to xylene and to maximize the catalyst selectivity towards the production of para-xylene. For instance, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 kilograms of feed per kilogram of catalyst per hour, at a pressure in the range of from about 100 kPa to 10,000 kPa, and in the presence of 0 to about 2 moles of hydrogen, more preferably from about 0.1 to about 2 moles of hydrogen per mole of organic compound, and optionally in the presence of 0 to 10 moles of nitrogen or another inert gas per mole of organic compound. This process is conducted for a period of time until a sufficient quantity of coke has deposited on the catalyst surface, generally at least about 2% by weight and more preferably from about 8% to about 40% by weight of coke. In a preferred embodiment, such a selectivation process is conducted in the presence of hydrogen in order to prevent rampant formation of coke on the catalyst. The initial mole ratio of hydrogen gas to toluene present in the toluene feed stream can be reduced during the selectivation process after a significant amount of coke has been deposited on the catalyst surface.

Selectivation of the catalyst can also be accomplished by treating the catalyst with a selectivation agent such as an organosilicon compound. Organosilicon compounds suitable for use as a selectivation agent are disclosed in U.S. Pat. No. 5,365,003, which is hereby incorporated by reference.

When used in the vapor phase disproportionation of toluene, the catalyst more preferably comprises particles of a first phase of MFI-type zeolite crystallites and a second binder phase of the MFI-type structurally adhered to the surfaces of the particles of the first phase. The particles of the first phase can have a micron average particle size from about 3 micrometers to about 4 micrometers and a silica to alumina mole ratio of from about 70 to about 80. The second binder phase can have an average particle size of less than about 0.1 micrometer and an alumina to silica ratio in the range from 300 to 10,000, preferably from 900 to 9,000.

Selectivated versions of the zeolite bound zeolite when used in vapor phase disproportionation exhibit a higher selectivity towards the production of para-xylene than conventional selectivated MFI catalysts.

Once the catalyst has been selectivated to the desired degree (e.g., greater than 80% para-xylene selectivity under the disproportionation conditions), reactor selectivation conditions are changed to disproportionation conditions. These disproportionation conditions can include a temperature from about 400° C. to about 550° C., more preferably from about 425° C. to about 510° C., at a hydrogen to toluene mole ratio of from 0 to about 10, preferably from about 0.1 to 5 and more preferably from about 0.1 to less than 1, at a pressure from about 1 atmosphere to about 100 atmospheres and utilizing WHSV of from about 0.5 to about 50. One of the particular advantages of the use of the catalyst in disproportionation is that it provides a good para-xylene selectivity at $H_2$/toluene mole ratios of less than 1, e.g., at about 0.5.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

Separation of the First Product Mixture

The first product mixture exiting the first reactor, as a result of reactions therein such as methylation and/or disproportionation, typically comprises toluene, para-xylene, meta-xylene, ortho-xylene, and optionally benzene. This mixture is separated in a first separation device such as a distillation column to obtain an upper effluent comprising toluene and optionally benzene, and a lower effluent comprising a mixture of xylene isomers. Where the first feed fed into the first reactor comprises benzene, and the reactions in the first reactor includes methylation, the first product mixture can comprises both benzene and toluene, and the upper effluent from the first separation device would typically comprise both toluene and benzene. Where the first feed fed into the first reactor comprises toluene but no benzene, and the reactions in the first reactor includes primarily methylation, the first product mixture may be essentially free of benzene, and the upper effluent from the first separation device would typically comprise toluene but no benzene or benzene at a very low concentration. When the first feed fed into the first reactor comprises toluene but no benzene, and the reactions in the first reactor includes primarily toluene disproportionation, the first product mixture typically comprises benzene, and the upper effluent from the first separation device would typically comprise both toluene and benzene. The upper effluent from the first separation device can be preferably recycled to the first reactor, whereby additional amount of xylenes can be produced therefrom. The upper effluent may be also harvested directly as a product stream, or further purified as a product stream. For example, where the upper effluent comprises substantially toluene, and the aromatic feed supplied to the first reactor is primarily benzene, the upper effluent may be collected as a toluene product stream if toluene is more valuable than benzene. On the other hand, where toluene is the primary aromatic feed to the first reactor, and the first reactor is a toluene disproportionation reactor, then the upper effluent may comprise primarily benzene, which can be harvested as a product stream or a precursor thereof, particularly if benzene is more valuable than toluene.

The lower effluent comprising xylene mixture may comprise mixed xylenes at substantially equilibrium concentrations at the temperature in the first reactor, or preferably comprise para-xylene at a concentration higher than the equilibrium concentration. Additional streams, such as light stream(s) comprising water, methanol, gas, and the like, and heavy stream(s) comprising ethylbenzene and C9+A, may be produced from the first separation device as well.

Separation of Para-xylene from Xylene Mixture

To obtain a pure para-xylene product from the mixed xylenes obtained from the first separation device, commercially available para-xylene separation devices may be used. These include simulated movable bed adsorption (SMBA) type and crystallization devices.

Variations of SMBA devices and processes useful for the present invention are available from, e.g., UOP, LLC, Des Plaines, Ill., U.S.A., and Axens, Rueil-Malmaison Cedex, France. U.S. Pat. No. 5,284,992 describes a variation of SMBA technology useful for the present invention in detail, the contents of which is incorporated herein by reference in their entirety.

Alternatively, conventional crystallization technology can be used alone or in combination with a SMBA device for separating para-xylene from the xylene mixture produced in the first reactor. Variations of such crystallization processes are described in, e.g., U.S. Pat. Nos. 3,067,270; 3,177,255; and 3,467,724, the contents of which are incorporated herein by reference in their entirety.

By using the SMBA and/or crystallizer devices, a high-purity para-xylene product comprising para-xylene at a concentration of at least c wt % can be obtained, where c can be 90, 91, 92, 93, 94, 95, 96, 97, 98, 99, or even higher. In addition, a meta-xylene and ortho-xylene-rich stream is obtained. The meta-xylene and ortho-xylene-rich stream may be substantially free of para-xylene, or comprise para-xylene at a very low concentration, e.g., lower than x wt %, where x can be 5, 4, 3, 2, 1, 0.5, or even 0.1, based on the total weight of the stream.

Para-xylene concentration in the mixed xylenes feed supplied to the SMBA and/or crystallizer separation device can significantly affect the energy efficiency of the separation device. Typically, a para-xylene concentration of at least Cpxy wt % in the feed, where Cpxy can be 50, 55, 60, 62, 64, 65, 66, 68, 70, 72, 74, 75, 76, 78, 80, 82, 84, or 85, is desired. As indicated by the examples below, the present invention enables a Cpxy significantly higher than the comparative technology using a liquid phase isomerization reactor instead of a transalkylation reactor. For example, in the present invention, the Cpxy can reach a level of at least 70. All other conditions being equal, the higher the Cpxy, the smaller the foot print of the SMBA device is required to produce the same amount of para-xylene in a given time, the higher the energy efficiency of the SMBA device, and the lower the operating cost of the SMBA. The SMBA device also typically utilizes a separation solvent. The higher the Cpxy, the smaller the amount of the separation solvent is needed. Typically, where a crystallizer is utilized for the para-xylene separation, the lower the Cpxy, the lower the operating temperature of the crystallizer is required to achieve the same output level of para-xylene, and hence the higher the energy cost. The present invention, by enabling a high Cpxy such as at least 70, enables the use of a single-stage crystallizer using a high-temperature refrigerant such as propane.

Xylene Transalkylation with Benzene and/or Toluene

To increase the total yield of para-xylene in the process of the present invention, the meta-xylene and ortho-xylene-rich stream from the xylene separation device is subjected to transalkylation in the second reactor with a transalkylation agent in the presence of a transalkylation catalyst. The transalkylation agent preferably comprises benzene and/or toluene at a total concentration thereof of at least d wt %, where d can be 90, 91, 92, 93, 94, 95, 96, 97, 98, 99, or 100. Preferably, the transalkylation agent is a feed comprising benzene at a concentration of at least d wt %, where d can be 90, 91, 92, 93, 94, 95, 96, 97, 98, 99, or 100.

WO 2013/095767A1 and EP 0276524 A1 describe xylene isomerization and transalkylation processes, the relevant portions thereof are incorporated herein by reference.

It is also possible to supply a methyl-rich material, such as C9+A hydrocarbons including but not limited to trimethylbenzenes, tetramethylbenzenes, and the like, into the transalkylation reactor. Such methyl-rich material can be a portion of the third feed or fed separated into the transalkylation reactor. This can be advantageous where the first reactor comprises a toluene disproportionation reactor, where the benzene produced from the toluene disproportionation reactor can be supply to the transalkylation reaction step to react with the methyl-rich feed.

The transalkylation catalyst can preferably comprise a solid acid material, such as a molecular sieve of the following framework types: MAZ, MEI, FAU, EMT, MFI, MEL, MTW, EUO, MTT, HEU, FER, TON, CHA, ERI, KFI, LEV, and LTA. Exemplary zeolite molecular sieves useful in the transalkylation catalysts include but are not limited to X-type, Y-type, ultrastable-Y, L-type, omega type and mordenite type zeolites with the latter being preferred. In addition to the solid acid component, the transalkylation catalyst may further comprise a hydrogenation metal component to promote the hydrogenation of certain olefins that may be present in the reaction system, either as impurities in the transalkylation feed or to in-situ generation as a result of side reactions. Accordingly, the transalkylation reaction conditions may preferably include supplying hydrogen into the transalkylation reactor. When the reactants contact each other on the surface of the catalyst, reactions occur resulting in the consumption of the reactants and the production of the desired products as well as byproducts.

The transalkylation reactions can be conducted primarily in liquid phase where a majority (by mole) of the reactants are in liquid state in the transalkylation reactor. When conducting the transalkylation reaction at an elevated temperature, e.g., at a temperature higher than 300° C., an elevated total internal pressure may be required in order to maintain liquid state of a majority of the reactants. In liquid phase transalkylation, the reaction conditions may include a temperature in a range from $T1°$ C. to $T2°$ C., and an absolute total internal pressure in a range from P1 kPa to P2 kPa, where T1 and T2 can be, independently, 100, 120, 140, 150, 160, 180, 200, 220, 240, 250, 260, 280, 300, 320, 340, 350, 360, 380, 400, 420, 440, 450, 460, 480, or 500, as long as T1<T2, and P1 and P2 can be, independently, 100, 200, 300, 400, 500, 600, 700, 800, 900, 1000, 2000, 3000, 4000, 5000, 6000, 7000, 8000, 9000, or 10,000, as long as P1<P2.

Alternatively, the transalkylation reactions can be conducted in vapor phase where, e.g., at least 80% (e.g., 85%, 88%, 90%, 91%, 92%, 93%, 94%, 95%, 96%, 97%, 98%, 99%, or even about 100%) by mole of the reactants are in vapor phase inside the reactor. Compared to liquid phase reactions, vapor phase transalkylation can be preferred because it can be conducted at a higher temperature and a lower pressure than liquid phase reactions, with fewer chances of side reactions and less byproducts produced. In vapor phase transalkylation, the reaction conditions may include a temperature in a range from $T3°$ C. to $T4°$ C., and an absolute total internal pressure in a range from P3 kPa to P4 kPa, where T3 and T4 can be, independently, 100, 120, 140, 150, 160, 180, 200, 220, 240, 250, 260, 280, 300, 320, 340, 350, 360, 380, 400, 420, 440, 450, 460, 480, 500, 520, 540, 550, 560, 580, or 600, as long as T3<T4, and P3 and P4 can be, independently, 100, 200, 300, 400, 500, 600, 700, 800, 900, 1000, 2000, 3000, 4000, 5000, 6000, 7000, 8000, 9000, or 10,000, as long as P3<P4.

As a result of the transalkylation reactions, some of the meta-xylene and ortho-xylene are converted to para-xylene. Preferably, the resultant reaction product mixture comprises toluene, and mixed xylenes at equilibrium concentrations under the transalkylation conditions. If benzene is used as a transalkylation agent with or without toluene, the transalkylation reaction mixture typically comprises some residual benzene as well.

The transalkylation reaction product mixture is separated in a third separation device such as a distillation column. A toluene-rich stream is obtained from the third separation device, which is then recycled to the first reaction step (e.g., alkylation and/or disproportionation step discussed above). A xylene-rich stream comprising mixed xylenes is obtained from the third separation device as well. The xylene-rich stream can be recycled, in part or in whole (e.g., 1%, 10%, 20%, 30%, 40%, 50%, 60%, 70%, 80%, 90%, 95%, 98%, 99%, or 100%), to the second separation device (a SMBA device or crystallization device as discussed above), where the para-xylene is at least partly separated and harvested as the product, and the meta-xylene and ortho-xylene are delivered to the transalkylation step again to produce more para-xylene. Alternatively or additionally, a part (e.g., 10%, 20%, 30%, 40%, 50%, 60%, 70%, 80%, 90%, 95%, 98%, or 99%) of the xylene-rich stream obtained from the third separation device can be recycled to the transalkylation step, whereby an additional amount of meta-xylene and ortho-xylene are converted into para-xylene. Still alternatively, where the transalkylation agent comprises, in whole or in part, benzene, all of the xylene-rich stream obtained from the third separation device may be recycled to the transalkylation step, whereby a majority, or even essentially all, of the xylenes supplied to the transalkylation step are converted into toluene, which is then recycled to the first reactor to produce more xylenes. Where the transalkylation agent comprises, in whole or in part, benzene, a benzene-rich stream is typically obtained from the third separation device, which can be recycled to the transalkylation reaction step. Likewise, depending on the relative value of benzene and/or benzene, one or both of them may be harvested from the third separation device as a product stream or a precursor thereof.

It is desired that among all aromatic feeds supplied into the transalkylation reactor, including the meta-xylene and ortho-xylene feed, the benzene feed, and any other feed, the molar ratio of all of the methyl groups and all the benzene rings (hereinafter M/R ratio) is in a range from Rx to Ry, where Rx and Ry can be 0.80, 0.85, 0.90, 0.92, 0.94, 0.95, 0.96, 0.98, 0.99, 1.00, 1.01, 1.02, 1.04, 1.05, 1.06, 1.08, 1.10, 1.15, or 1.20, as long as Rx<Ry. More preferably, the M/R ratio is maintained in a range from 0.95 to 1.10. Most preferably, the M/R ratio is maintained in a range from 0.98 to 1.05. A M/R ratio higher than 1.20 can lead to the production of overally high quantity of trimethylbenzenes, which are highly undesirable C9+A byproducts. A M/R ratio lower than 0.80 would result in less than optimal conversion of benzene in the reactor. For the purpose of the present invention, a mole of a feed compound comprising m benzene ring(s) and n methyl group(s) in each molecule thereof comprises m moles of benzene ring(s) and n moles of methyl group(s). Thus, for the purpose of calculating the M/R ratio in a feed herein, one mole of benzene comprises one mole of benzene rings and zero mole of methyl group; one mole of toluene comprises one mole of benzene rings and one mole of methyl groups; one mole of para-xylene (or meta-xylene or ortho-xylene) comprises one mole of benzene rings and two moles of methyl groups; and one mole of 1,3,5-trimethylbenzene comprises one mole of benzene rings and 3 moles of methyl groups.

It has been surprisingly found that where the transalkylation agent comprises primarily benzene (e.g., at least 90 wt % as described above), compared to recycling a part or all of the xylene-rich stream from the third separation device to the second separation step, it is preferred that all of the xylene-rich stream obtained from the third separation device is recycled to the transalkylation step. This is because the latter resulted in higher yield of para-xylene at the same level of raw material costs and energy consumption.

It has also been found that, where benzene and toluene constitute a great majority of all of the fresh aromatic feeds (e.g., at least 90 wt %, such as 91 wt %, 92 wt %, 93 wt %, 94 wt %, 95 wt %, 96 wt %, 97 wt %, 98 wt %, 99 wt %, or even essentially 100 wt %) among all the feeds (including the first, second, and the third feeds discussed above) supplied to the process of the present invention, where the molar ratio of benzene to toluene (hereinafter B/T ratio) is at least 1.0, it is preferred that at least 50% of the mixed xylenes produced from the transalkylation reactor (i.e., the second reactor, R2) is recycled to the transalkylation reactor. This would result in the production of higher amount of toluene compared to feeding more of the mixed xylenes produced from the transalkylation reactor to the second separation device. The higher the B/T ratio among all the fresh feeds, the more desirable to recycle a higher percentage of the mixed xylenes produced from the transalkylation reactor to the transalkylation reactor. On the other hand, where the B/T ratio is at most 1.0, it is preferred that at least 50% of the mixed xylenes produced from the transalkylation reactor (i.e., the second reactor, R2) is delivered to the second separation device. This would result in the feeding of higher total amount of mixed xylenes to the second separation device.

Figure 4:
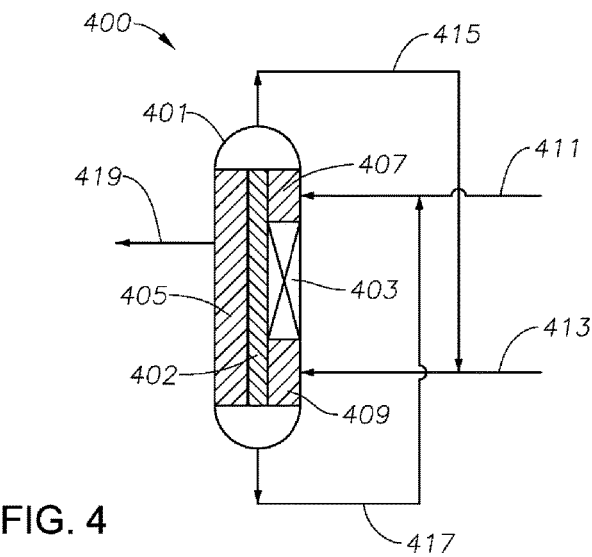
FIG. 4 is a schematic diagram showing a reactive distillation column transalkylation reactor in operation in exemplary processes of the present invention.

Preferably, a reactive distillation column transalkylation reactor is used in the process of the present invention. FIG. 4 schematically illustrates an exemplary reactive distillation column 400 in operation. The column comprises a shell 401 defining an internal space, an internal dividing wall 402 partitioning the internal space into a reaction zone (403, 407, and 409) on the right side, and a distillation zone 405 on the left side. The dividing wall 402 (e.g., a steel plate) is preferably impermeable to the reaction mixture. However, above and below the dividing wall 402, fluid is allowed to flow between the reaction zone and the distillation zone. The reaction zone comprises a transalkylation catalyst bed 403, a upper section 407 above bed 403 and a lower section 409 below bed 403 having inert packing materials and/or trays. The distillation zone 405 is loaded with packing materials and/or trays. A meta-xylene and/or ortho-xylene-rich stream 411 is fed to the reaction zone, preferably above the catalyst bed 403, and a fresh benzene-rich stream 413 is fed to the reaction zone below the stream 411, preferably below the catalyst bed 403. The temperature profile inside the column is set in a manner such that benzene vaporizes at least partially and travels upwards in the reaction zone, while the xylene molecules travel downwards and contact the rising benzene molecules on the surface of the catalyst, whereby transalkylation reactions occur accordingly to produce a mixture of benzene, toluene, and mixed xylenes. The xylenes are enriched at the bottom of the column and drawn as a bottoms effluent 417. Benzene and toluene enter into the distillation zone, where the temperature profile is such that a high-purity toluene stream 419 (at least 90 wt % pure, e.g.,) can be drawn from the side thereof. A substantially pure benzene top stream 415 can be obtained, and combined with fresh benzene stream 413 to be delivered to the reaction zone. As shown, the xylene-rich bottom effluent 417 can be completely recycled to the column, combined with the meta-xylene and/or ortho-xylene-rich stream 411 and delivered to the reaction zone. In the process set-forth in FIG. 4, essentially all of the xylenes supplied from transalkylation feed 411 are converted into toluene. The toluene stream 419 can be recycled to the first reactor (e.g., an alkylation or disproportionation reactor) to produce additional amount of xylenes. Alternatively, a part or the entirety of the xylene-rich stream 417 can be delivered to the second separation device (a SMBA or crystallizer device) to harvest at least a portion of the para-xylene therein. The reactive distillation column functions as a both a transalkylation reactor and a distillation column, and is therefore preferred. The reaction conditions in the reaction zone can include a temperature in a range from T5° C. to T6° C., and an absolute total internal pressure in a range from P5 kPa to P6 kPa, where T5 and T6 can be, independently, 100, 120, 140, 150, 160, 180, 200, 220, 240, 250, 260, 280, 300, 320, 340, 350, 360, 380, 400, 420, 440, 450, 460, 480, 500, 520, 540, 550, 560, 580, or 600, as long as T5<T6, and P5 and P6 can be, independently, 100, 200, 300, 400, 500, 600, 700, 800, 900, 1000, 2000, 3000, 4000, 5000, 6000, 7000, 8000, 9000, or 10,000, as long as P5<P6.

EXAMPLES AND DESCRIPTION ACCORDING TO THE DRAWINGS

The present invention is further illustrated by the following non-limiting examples referencing the relevant schematic drawings. It should be noted that all these examples are based on simulation, not actual operation in a lab, a pilot plant or a production plant. Thus, some of the devices (e.g., mixing devices) described in these examples and shown in the drawings may not be required in real production. One having ordinary skill in the art should understand that routine equipment, such as valves, pumps, heat exchangers, boilers, furnaces, and the like, though not shown or described herein, may be added in real production following the general principles and schematics described herein.

In the tables in and description of the examples below, "p-X" means para-xylene, "m-X" means meta-xylene, "o-X" means ortho-xylene, "gas" means hydrocarbons and derivatives thereof having boiling points lower than benzene, and C9+A means aromatic compounds having at least 9 carbon atoms, including but not limited to trimethylbenzenes, methylethylbenzenes, biethylbenzenes, tetraethylbenzenes, methylpropylbenzenes, and the like.

Example 1 (Comparative)

FIG. 1 schematically shows the process flow 100 of a comparative example differing from the present invention. In this process, a feed stream 101 comprising gas, water, and fresh methanol, toluene and benzene is fed into a mixing device M1, where it is mixed with a recycle stream 106 comprising benzene and toluene to form a combined stream 103, which is delivered into an alkylation reactor R1. In R1, benzene and toluene react with methanol in the presence of an alkylating catalyst such as a zeolite molecular sieve, to obtain a first reaction product mixture stream 105 comprising benzene, toluene, and mixed xylenes. Stream 105 is delivered into a first separation device S1 (a distillation tower), where a light stream 106 comprising benzene and toluene, and a xylene stream 107 comprising the xylenes are produced. Additional streams, collectively referred to as stream 108, that may comprise one or more of gas, water, ethylbenzene, and C9+A, may be produced from S1 as well. Stream 106 is recycled to the mixing device M1, and stream 107 is delivered to a second mixing device M2, where it is mixed with a stream 119 comprising mixed xylenes to obtain a combined stream 109. Stream 109 is then delivered to a second separation device S2, which can be a simulated moving bed adsorption (SMBA) type device (such as Parex® separation device available from UOP LLC, Des Plaines, Ill., U.S.A.), where a product stream 110 comprising para-xylene at a concentration of at least 90 wt % and a stream 111 comprising primarily meta-xylene and ortho-xylene are obtained. Alternatively, a crystallizer may be used in lieu of or in combination with the SMBA device as the separation device S2. Stream 111 is then fed to a third separation device S3 (a distillation tower, e.g.), where a xylene stream 113 rich in meta-xylene and ortho-xylene is produced. An optional purge stream 115 comprising ethylbenzene and C9+A, usually small in quantity if produced at all, may be produced from S3 as a byproduct stream or discarded as waste. Stream 113 is subsequently delivered to a reactor R2, where isomerization reactions occur primarily in liquid state in the presence of an isomerization catalyst. The isomerization reaction product stream 117, which preferably comprises mixed xylenes at equilibrium concentrations under the reaction conditions, is then fed to a fourth separation device S4 such as a distillation tower. Stream 119 produced from S4, comprising mixed xylenes, is delivered to the second mixing device M2, where it is combined with stream 107 to form xylene stream 109, as described above. An optional purge stream 121 comprising ethylbenzene and C9+A, usually small in quantity if produced at all, may be produced from S4 as a byproduct stream or discarded as waste.

The amounts of the various components in the respective streams in this process are calculated and given below in TABLE I. In stream 109 fed to the separation device S2, the concentration of para-xylene is about 53 wt %.

Example 2 (Inventive)

Figure 2:
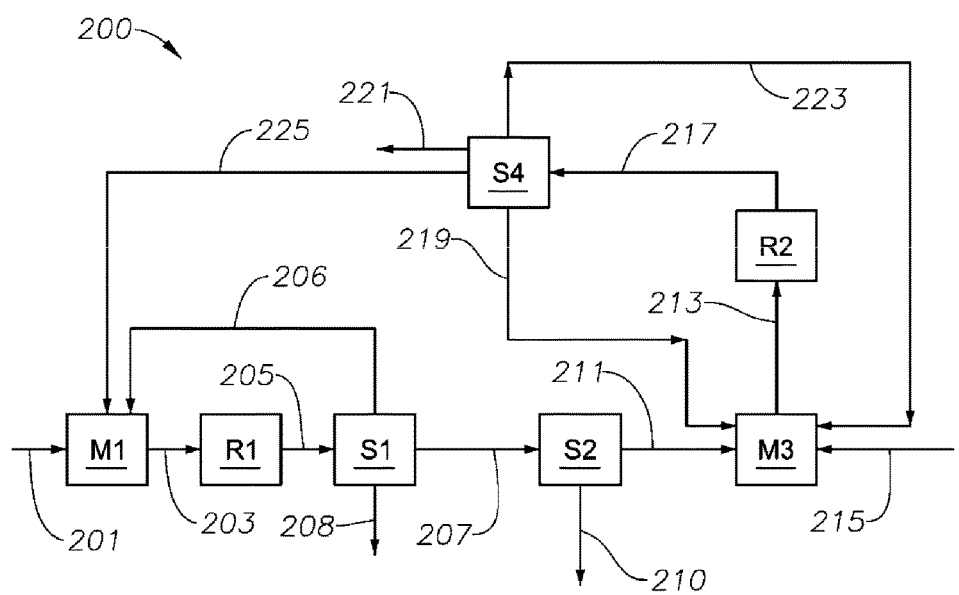
FIGS. 2 and 3 are schematic diagrams showing exemplary processes for making para-xylene according to the present invention from benzene and/or toluene, optionally with a methylation agent, including a step of methylation and/or disproportionation, a step of separation of xylene mixture to obtain a para-xylene product, and a step of transalkylation between meta-xylene/ortho-xylene and benzene/toluene.

FIG. 2 schematically shows a process flow 200 of the present invention. In this process, a feed stream 201 comprising water, gas, and fresh methanol and toluene and/or benzene is fed into a mixing device M1, where it is mixed with a recycle stream 206 comprising toluene and a recycle stream 225 comprising toluene to form a combined stream 203, which is delivered into an alkylation reactor R1. In R1, toluene and/or benzene react with methanol in the presence of an alkylating catalyst such as a zeolite molecular sieve, to obtain a first reaction product mixture stream 205 comprising toluene, mixed xylenes and optionally benzene. Stream 205 is delivered into a first separation device S1 (a distillation tower), where a light stream 206 comprising toluene and optionally benzene and a xylene stream 207 comprising mixed xylenes are produced. Other streams, collectively referred to as stream 208, which may include gas, water, heavies such as C9+A, may be produced from S1 as well. Stream 206 is recycled to the mixing device M1, and stream 207 is delivered to a separation device S2, which can be a simulated moving bed adsorption (SMBA) type device (such as Parex® separation device available from UOP LLC, Des Plaines, Ill., U.S.A.), where a product stream 210 comprising para-xylene at a concentration of at least 90 wt % and a stream 211 comprising primarily meta-xylene and ortho-xylene are obtained. Alternatively, a crystallizer may be used in lieu of or in addition to the SMBA device as S2. Stream 211 is then fed to a third mixing device M3, where it is combined with a fresh benzene stream 215 and a stream 219 (described in detail below) comprising mixed xylenes, to form a stream 213 and delivered to a second reactor R2, where transalkylation reactions between and among benzene, toluene, and the xylenes occur primarily in liquid state in the presence of a transalkylation catalyst such as a zeolite. The transalkylation reaction product stream 217, which preferably comprises benzene, toluene, and mixed xylenes at equilibrium concentrations under the reaction conditions, is then fed to a separation device S4 such as a distillation tower, to produce a benzene-containing stream 223, a toluene-rich stream 225, and a xylene-rich stream 219. An optional purge stream 221, which may comprise ethylbenzene and C9+A, usually at a small quantity if produced at all, may be produced from S4 as well. The toluene-rich stream 225 is recycled to M1. Stream 219 is recycled to M3, combined with fresh benzene stream 215 and meta-xylene and ortho-xylene stream 211 to form stream 213, and then delivered to reactor R2, as described above.

The amounts of the various components in the respective streams in this process are calculated and given below in TABLE II. In stream 207 fed to the separation device S2, the concentration of para-xylene is about 80 wt %, which is much higher than the para-xylene concentration in feed stream 109 in FIG. 1 in Example 1. Therefore, compared to Example 1, for a system with substantially the same para-xylene output, a separation device with a much smaller size using a much smaller quantity of separation agent can be used in Example 2. To obtain the same separation efficiency (i.e., percentage of para-xylene separated relative to the total amount of para-xylene in the feed to the separation device), a much higher refrigeration temperature (e.g., using propane as the refrigerant instead of ethylene or ammonia) can be used in Example 2 compared to Example 1, if a crystallizer is used as the second separation device S2 or a part thereof. In addition, in Example 2, a single-stage refrigeration may be sufficient while in Example 1 a two-stage refrigeration may be required. Accordingly, the process of Example 2 is preferred over Example 1.

Example 3 (Inventive)

Figure 3:
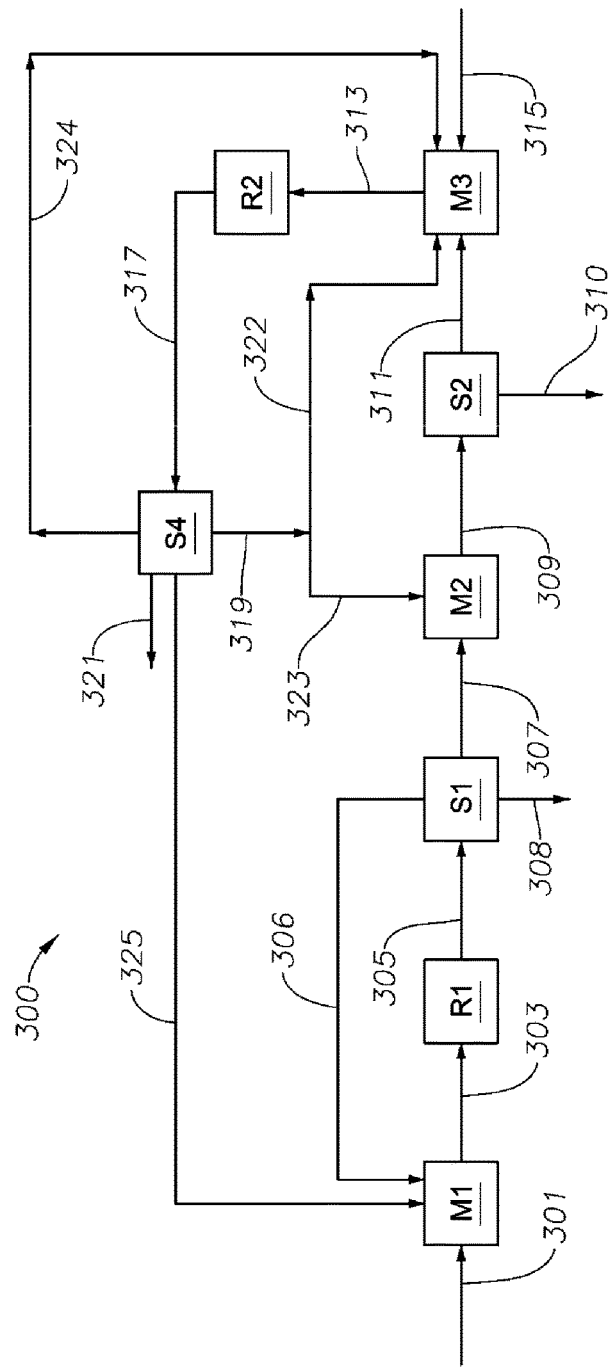

FIG. 3 schematically shows a process flow 300 of the present invention. In this process, a feed stream 301 comprising gas, water, and fresh methanol and toluene and/or benzene is fed into a mixing device M1, where it is mixed with a recycle stream 306 comprising toluene and a recycle stream 325 comprising toluene to form a combined stream 303, which is delivered into an alkylation reactor R1. In R1, toluene and/or benzene, if any, reacts with methanol in the presence of an alkylating catalyst such as a zeolite molecular sieve, to obtain a first reaction product mixture stream 305 comprising toluene and mixed xylenes. Stream 305 is delivered into a first separation device S1 (a distillation tower), where a light stream 306 comprising toluene and optionally benzene and a xylene stream 307 comprising mixed xylenes are produced. Additional streams, collectively referred to as 308, comprising one or more of gas, water, ethylbenzene, and C9+A, may be produced from S1 as well. Stream 306 is recycled to the mixing device M1. Stream 307 is delivered to a second mixing device M2, where it is combined with a stream 323 (if present) comprising mixed xylenes to form stream 309. Stream 309 is then delivered to a second separation device S2, which can be a simulated moving bed adsorption (SMBA) type device (such as, Parex® separation device available from UOP LLC, Des Plaines, Ill., U.S.A.), where a product stream 310 comprising para-xylene at a concentration of at least 90 wt % and a stream 311 comprising primarily meta-xylene and ortho-xylene are obtained. Alternatively, a crystallizer may be used in lieu of or in addition to the SMBA device as the separation device S2. Stream 311 is then fed to a third mixing device M3, where it is combined with a fresh benzene stream 315, a recycle benzene stream 324 (described below), and a mixed xylenes stream 322 (if present) to form a stream 313. Stream 313 is then delivered to a second reactor R2, where transalkylation reactions among benzene, toluene, and the xylenes occur primarily in liquid state in the presence of a transalkylation catalyst such as a zeolite molecular sieve. The transalkylation reaction product stream 317, which preferably comprises benzene, toluene, and mixed xylenes at equilibrium concentrations under the reaction conditions, is then fed to a subsequent separation device S4 such as a distillation tower, to produce a benzene-containing stream 324, a toluene-rich stream 325, and a mixed xylene-rich stream 319. Stream 324 is recycled to M3, as described above. Stream 319 is optionally divided into two streams 322 and 323, with stream 323 delivered to M2, and stream 322 delivered to M3, as described above (in this Example as shown in TABLE III, 100% of stream 319 is delivered to M2 and subjected to separation in S2). Thus, a part or the entirety of stream 319 from S4 may be delivered to either of M2 or M3. Toluene-rich stream 325 is recycled to M1.

The amounts of the various components in the respective streams in this example are calculated and given below in TABLE III. In stream 309 fed to the separation device S2, the concentration of para-xylene is about 80 wt %, which is much higher than the para-xylene concentration in feed stream 109 in FIG. 1 in Example 1. To obtain the same separation efficiency, a much higher refrigeration temperature (e.g., using propane as the refrigerant instead of ethylene or ammonia) can be used in Example 3 compared to Example 1, if a crystallizer is used as the second separation device S2 or a part thereof. In addition, in Example 3, a single-stage refrigeration may be sufficient while in Example 1 a two-stage refrigeration may be required. Therefore, compared to Example 1, for a system with substantially the same para-xylene output, a separation device with a much smaller size using a much smaller quantity of separation agent can be used in Example 3. This can reduce the cost of the equipment and operation of the separation step. Accordingly, Example 3 is a preferred process compared to Example 1.

Example 4 (Comparative)

The system set-up in this example is the same as in Example 1, except that the composition of the feed supplied to the first mixing device M1 is different.

The amounts of the various components in the respective streams in this process are calculated and given below in TABLE IV. In stream 109 fed to the separation device S2, the concentration of para-xylene is about 53 wt %.

Example 5 (Inventive)

The system set-up in this example is the same as in Example 3, except that (i) the benzene/toluene molar ratio in the total fresh feeds to the mixing devices M1 and M3 is different; and (ii) stream 319 is divided into two streams 322 and 323, with the weight ratio of stream 322 to stream 323 being about 3. Thus, about 75 wt % of the mixed xylenes produced from the transalkylation reactor R2 is recycled to R2, and the remainder 25 wt % to the second mixing device M2, and subsequently subjected to separation in the second separation device S2. The quantities of the benzene and toluene feeds in this example are identical with those in Example 4 above.

The amounts of the various components in the respective streams in this process are calculated and given below in TABLE V. In stream 309 fed to the separation device S2, the concentration of para-xylene is about 76 wt %, which is much higher than the para-xylene concentration in feed stream 109 in Example 4. Therefore, compared to Example 4, for a system with substantially the same para-xylene output, a separation device with a much smaller size can be used in Example 5. To obtain the same separation efficiency, a much higher refrigeration temperature (e.g., using propane as the refrigerant instead of ethylene or ammonia) can be used in Example 5 compared to Example 4, if a crystallizer is used as the second separation device S2. In addition, in Example 5, a single-stage refrigeration may be sufficient while in Example 4 a two-stage refrigeration may be required. Accordingly, the process of Example 5 is preferred over that in Example 4.

Example 6 (Comparative)

The system set-up in this example is the same as in Example 1, except that the composition of the feed supplied to the first mixing device M1 is different.

The amounts of the various components in the respective streams in this process are calculated and given below in TABLE VI. In stream 109 fed to the separation device S2, the concentration of para-xylene is about 53 wt %.

Example 7 (Inventive)

The system set-up in this example is the same as in Example 3, except that (i) the benzene/toluene molar ratio in the total fresh feeds to the mixing devices M1 and M3 is different; and (ii) stream 319 is divided into two streams 322 and 323, with the weight ratio of stream 322 to stream 323 being about 1. Thus, about 50 wt % of the mixed xylenes produced from the transalkylation reactor R2 is recycled to R2, and the remainder 50 wt % to the second mixing device M2, and subsequently subjected to separation in the second separation device S2. The quantities of the benzene and toluene feeds in this example are identical with those in Example 6 above.

The amounts of the various components in the respective streams in this process are calculated and given below in TABLE VII. In stream 309 fed to the separation device S2, the concentration of para-xylene is about 76 wt %, which is much higher than the para-xylene concentration in feed stream 109 in Example 6. Therefore, compared to Example 6, for a system with substantially the same para-xylene output, a separation device with a much smaller size can be used in Example 7. To obtain the same separation efficiency, a much higher refrigeration temperature (e.g., using propane as the refrigerant instead of ethylene or ammonia) can be used in Example 7 compared to Example 6, if a crystallizer is used as the second separation device S2. In addition, in Example 7, a single-stage refrigeration may be sufficient while in Example 6 a two-stage refrigeration may be required. Accordingly, the process of Example 7 is preferred over that in Example 6.

Example 8 (Comparative)

The system set-up in this example is the same as in Example 1, except that the composition of the feed supplied to the first mixing device M1 is different.

The amounts of the various components in the respective streams in this process are calculated and given below in TABLE VIII. In stream 109 fed to the separation device S2, the concentration of para-xylene is about 53 wt %.

Example 9 (Inventive)

The system set-up in this example is the same as in Example 3, except that (i) the benzene/toluene molar ratio in the total fresh feeds to the mixing devices M1 and M3 is different; and (ii) stream 319 is divided into two streams 322 and 323, with the weight ratio of stream 322 to stream 323 being about ⅓. Thus, about 25 wt % of the mixed xylenes produced from the transalkylation reactor R2 is recycled to R2, and the remainder 75 wt % to the second mixing device M2, and subsequently subjected to separation in the second separation device S2. The quantities of the benzene and toluene feeds in this example are identical with those in Example 8 above.

The amounts of the various components in the respective streams in this process are calculated and given below in TABLE IX. In stream 309 fed to the separation device S2, the concentration of para-xylene is about 74 wt %, which is much higher than the para-xylene concentration in feed stream 109 in Example 8. Therefore, compared to Example 8, for a system with substantially the same para-xylene output, a separation device with a much smaller size can be used in Example 9. To obtain the same separation efficiency, a much higher refrigeration temperature (e.g., using propane as the refrigerant instead of ethylene or ammonia) can be used in Example 9 compared to Example 8, if a crystallizer is used as the second separation device S2. In addition, in Example 9, a single-stage refrigeration may be sufficient while in Example 8 a two-stage refrigeration may be required. Accordingly, the process of Example 9 is preferred over that in Example 8.

Example 10 (Comparative)

The system set-up in this example is the same as in Example 1, except that the composition of the feed supplied to the first mixing device M1 is different.

The amounts of the various components in the respective streams in this process are calculated and given below in TABLE X. In stream 109 fed to the separation device S2, the concentration of para-xylene is about 53 wt %.

Example 11 (Inventive)

The system set-up in this example is the same as in Example 3, except that (i) the benzene/toluene molar ratio in the total fresh feeds to the mixing devices M1 and M3 is different; and (ii) stream 319 is entirely delivered to the second mixing device M2, and subsequently subjected to separation in the second separation device S2. The quantities of the benzene and toluene feeds in this example are identical with those in Example 10 above.

The amounts of the various components in the respective streams in this process are calculated and given below in TABLE XI. In stream 309 fed to the separation device S2, the concentration of para-xylene is about 76%, which is much higher than the para-xylene concentration in feed stream 109 in Example 10. Therefore, compared to Example 10, for a system with substantially the same para-xylene output, a separation device with a much smaller size can be used in Example 11. To obtain the same separation efficiency, a much higher refrigeration temperature (e.g., using propane as the refrigerant instead of ethylene or ammonia) can be used in Example 11 compared to Example 10, if a crystallizer is used as the second separation device S2. In addition, in Example 11, a single-stage refrigeration may be sufficient while in Example 10 a two-stage refrigeration may be required. Accordingly, the process of Example 11 is preferred over that in Example 10.

As indicated above, the mixed xylene exiting the transalkylation reactor R2 can be delivered, in whole or in part, either to the second separation device (the SMBA device and/or crystallizer) where para-xylene is harvested, or to the transalkylation reactor R2, where toluene can be produced from the transalkylation between benzene and the xylenes. Generally, if the B/T ratio among the aromatic feed(s) to the first reactor (R1, an alkylation reactor in the above examples) and the feed(s) to the second reactor (R2, a transalkylation reactor in the above examples) is at least one, it is preferred that at least 50 wt % of the mixed xylenes exiting R2 is recycled to R2. On the other hand, if the B/T molar ratio is at most one, it is preferred that at least 50 wt % of the mixed xylenes exiting R2 is delivered to the second separation device S2. Preferably, in all the feeds supplied to the transalkylation reactor R2, the M/R ratio is in a range from Rx to Ry, where Rx and Ry can be 0.80, 0.85, 0.90, 0.92, 0.94, 0.95, 0.96, 0.98, 0.99, 1.00, 1.01, 1.02, 1.04, 1.05, 1.06, 1.08, 1.10, 1.15, or 1.20, as long as Rx<Ry. More preferably, the M/R ratio is maintained in a range from 0.95 to 1.10. Most preferably, the M/R ratio is maintained in a range from 0.98 to 1.05.

As indicated by the above examples, the present invention can significantly increase the para-xylene concentration in the feed to the second separation device (by 31% to 52% as shown in the examples for SMBA devices), thereby significantly reduce the energy consumption by the second separation device. If a single step crystallizer is used as the second separation device, the para-xylene recovery can be increased from 56.0% to 87.8% (57% improvement).

Figure 5:
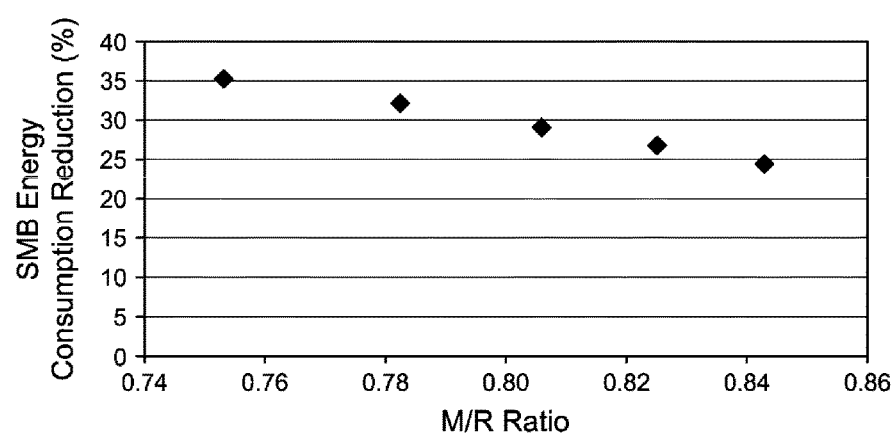
FIG. 5 is a diagram showing the energy consumption reduction of a SMBA device used for separating para-xylene from mixed xylenes by using the process of the present invention as a function of the molar ratio of methyl groups to benzene rings among all aromatic feeds supplied to the process.

Energy consumption reductions (%) by a SMBA device according to the present invention compared to the comparative examples are calculated at various M/R ratios, and are presented in FIG. 5. In the above examples, energy consumption can be reduced by up to 36% by reducing the raffinate flow in the SMBA unit. Clearly, the higher the M/R ratio in the total feeds, the higher the energy consumption reduction at the SMBA separation device. It is believed that comparable benefits can be achieved if a crystallizer is used in lieu of the SMBA device as the second separation device.

TABLE I (Example 1, Comparative)

Weight in Stream (Parts)

| Component | 101 | 103 | 105 | 106 | 107 | 108 | 109 | 110 | 111 | 113 | 115 | 117 | 119 | 121 |
|---|---|---|---|---|---|---|---|---|---|---|---|---|---|---|
| Methanol | 88 | 100 | 12 | 12 | 0 | 0 | 0 | 0 | 0 | 0 | 0 | 0 | 0 | 0 |
| Gas/$H_2O$ | 45 | 45 | 111 | 0 | 0 | 111 | 0 | 0 | 0 | 0 | 0 | 0 | 0 | 0 |
| Benzene | 28 | 73 | 45 | 45 | 0 | 0 | 0 | 0 | 0 | 0 | 0 | 0 | 0 | 0 |
| Toluene | 100 | 346 | 246 | 246 | 0 | 0 | 0 | 0 | 0 | 0 | 0 | 0 | 0 | 0 |
| p-X | 0 | 0 | 117 | 0 | 117 | 0 | 147 | 143 | 4 | 4 | 0 | 30 | 30 | 0 |
| m-X + o-X | 0 | 0 | 29 | 0 | 29 | 0 | 131 | 0 | 131 | 129 | 3 | 102 | 102 | 0 |
| C9 + A | 0 | 0 | 5 | 0 | 0 | 5 | 0 | 0 | 0 | 0 | 0 | 0 | 0 | 0 |
| Total | 261 | 564 | 564 | 303 | 145 | 115 | 278 | 143 | 135 | 133 | 3 | 133 | 132 | 0 |

TABLE II (Example 2, Inventive)

Weight in Stream (Parts)

| Component | 201 | 203 | 205 | 206 | 207 | 208 | 110 | 211 | 213 | 215 | 217 | 219 | 221 | 223 | 225 |
|---|---|---|---|---|---|---|---|---|---|---|---|---|---|---|---|
| Methanol | 87 | 99 | 12 | 12 | 0 | 0 | 0 | 0 | 0 | 0 | 0 | 0 | 0 | 0 | 0 |
| Gas/$H_2O$ | 45 | 45 | 109 | 0 | 0 | 109 | 0 | 0 | 0 | 0 | 0 | 0 | 0 | 0 | 0 |
| Benzene | 0 | 0 | 0 | 0 | 0 | 0 | 0 | 0 | 65 | 28 | 37 | 0 | 0 | 37 | 0 |
| Toluene | 100 | 428 | 265 | 265 | 0 | 0 | 0 | 0 | 0 | 0 | 63 | 0 | 0 | 0 | 63 |
| p-X | 0 | 0 | 144 | 0 | 144 | 0 | 143 | 1 | 11 | 0 | 10 | 10 | 0 | 0 | 0 |
| m-X + o-X | 0 | 0 | 36 | 0 | 36 | 0 | 0 | 36 | 75 | 0 | 40 | 40 | 0 | 0 | 0 |
| C9 + A | 0 | 0 | 6 | 0 | 0 | 6 | 0 | 0 | 0 | 0 | 2 | 0 | 2 | 0 | 0 |
| Total | 232 | 572 | 572 | 277 | 180 | 114 | 143 | 37 | 151 | 28 | 151 | 50 | 2 | 37 | 63 |

TABLE III (Example 3, Inventive) (PA-0)

Weight in Stream (Parts)

| Component | 301 | 303 | 305 | 306 | 307 | 308 | 309 | 310 | 311 | 313 | 315 | 317 | 319 | 321 | 322 | 323 | 324 | 325 |
|---|---|---|---|---|---|---|---|---|---|---|---|---|---|---|---|---|---|---|
| Methanol | 87 | 99 | 12 | 12 | 0 | 0 | 0 | 0 | 0 | 0 | 0 | 0 | 0 | 0 | 0 | 0 | 0 | 0 |
| Gas/$H_2O$ | 45 | 45 | 109 | 0 | 0 | 109 | 0 | 0 | 0 | 0 | 0 | 0 | 0 | 0 | 0 | 0 | 0 | 0 |
| Benzene | 0 | 0 | 0 | 0 | 0 | 0 | 0 | 0 | 0 | 65 | 28 | 37 | 0 | 0 | 0 | 0 | 37 | 0 |
| Toluene | 100 | 428 | 265 | 265 | 0 | 0 | 0 | 0 | 0 | 0 | 0 | 63 | 0 | 0 | 0 | 0 | 0 | 63 |
| p-X | 0 | 0 | 144 | 0 | 144 | 0 | 144 | 143 | 1 | 11 | 0 | 10 | 10 | 0 | 10 | 0 | 0 | 0 |
| m-X + o-X | 0 | 0 | 36 | 0 | 36 | 0 | 36 | 0 | 36 | 75 | 0 | 40 | 40 | 0 | 40 | 0 | 0 | 0 |
| C9 + A | 0 | 0 | 6 | 0 | 0 | 6 | 0 | 0 | 0 | 0 | 0 | 2 | 0 | 2 | 0 | 0 | 0 | 0 |
| Total | 232 | 572 | 572 | 277 | 180 | 114 | 180 | 143 | 37 | 151 | 28 | 151 | 50 | 2 | 50 | 0 | 37 | 63 |

TABLE IV (Example 4, Comparative) (PA-25)

Weight in Stream (Parts)

| Component | 101 | 103 | 105 | 106 | 107 | 108 | 109 | 110 | 111 | 115 | 116 | 119 | 120 | 121 |
|---|---|---|---|---|---|---|---|---|---|---|---|---|---|---|
| Methanol | 83 | 94 | 11 | 11 | 0 | 0 | 0 | 0 | 0 | 0 | 0 | 0 | 0 | 0 |
| Gas/$H_2O$ | 42 | 42 | 104 | 0 | 0 | 104 | 0 | 0 | 0 | 0 | 0 | 0 | 0 | 0 |
| Benzene | 24 | 62 | 39 | 39 | 0 | 0 | 0 | 0 | 0 | 0 | 0 | 0 | 0 | 0 |
| Toluene | 100 | 333 | 233 | 233 | 0 | 0 | 0 | 0 | 0 | 0 | 0 | 0 | 0 | 0 |

TABLE IV-continued (Example 4, Comparative) (PA-25)

Weight in Stream (Parts)

| Component | 101 | 103 | 105 | 106 | 107 | 108 | 109 | 110 | 111 | 115 | 116 | 119 | 120 | 121 |
|---|---|---|---|---|---|---|---|---|---|---|---|---|---|---|
| p-X | 0 | 0 | 112 | 0 | 112 | 0 | 141 | 137 | 4 | 4 | 0 | 29 | 29 | 0 |
| m-X + o-X | 0 | 0 | 28 | 0 | 28 | 0 | 127 | 0 | 127 | 124 | 3 | 99 | 99 | 0 |
| C9 + A | 0 | 0 | 5 | 0 | 0 | 5 | 0 | 0 | 0 | 0 | 0 | 0 | 0 | 0 |
| Total | 249 | 532 | 532 | 283 | 140 | 109 | 268 | 137 | 130 | 128 | 3 | 128 | 128 | 0 |

TABLE V (Example 5, Inventive) (PA-25)

Weight in Stream (Parts)

| Component | 301 | 303 | 305 | 306 | 307 | 308 | 309 | 310 | 311 | 313 | 315 | 317 | 319 | 321 | 322 | 323 | 324 | 325 |
|---|---|---|---|---|---|---|---|---|---|---|---|---|---|---|---|---|---|---|
| Methanol | 83 | 94 | 11 | 11 | 0 | 0 | 0 | 0 | 0 | 0 | 0 | 0 | 0 | 0 | 0 | 0 | 0 | 0 |
| Gas/$H_2O$ | 42 | 42 | 103 | 0 | 0 | 103 | 0 | 0 | 0 | 0 | 0 | 0 | 0 | 0 | 0 | 0 | 0 | 0 |
| Benzene | 0 | 0 | 0 | 0 | 0 | 0 | 0 | 0 | 0 | 56 | 24 | 32 | 0 | 0 | 0 | 0 | 32 | 0 |
| Toluene | 100 | 407 | 252 | 252 | 0 | 0 | 0 | 0 | 0 | 0 | 0 | 55 | 0 | 0 | 0 | 0 | 0 | 55 |
| p-X | 0 | 0 | 137 | 0 | 137 | 0 | 139 | 138 | 1 | 8 | 0 | 9 | 9 | 0 | 7 | 2 | 0 | 0 |
| m-X + o-X | 0 | 0 | 34 | 0 | 34 | 0 | 43 | 0 | 43 | 69 | 0 | 35 | 35 | 0 | 26 | 9 | 0 | 0 |
| C9 + A | 0 | 0 | 6 | 0 | 0 | 6 | 0 | 0 | 0 | 0 | 0 | 2 | 0 | 2 | 0 | 0 | 0 | 0 |
| Total | 225 | 544 | 544 | 264 | 171 | 109 | 182 | 138 | 44 | 133 | 24 | 133 | 44 | 2 | 33 | 11 | 32 | 55 |

TABLE VI (Example 6, Comparative) (PA-50)

Weight in Stream (Parts)

| Component | 101 | 103 | 105 | 106 | 107 | 108 | 109 | 110 | 111 | 115 | 116 | 119 | 120 | 121 |
|---|---|---|---|---|---|---|---|---|---|---|---|---|---|---|
| Methanol | 79 | 90 | 11 | 11 | 0 | 0 | 0 | 0 | 0 | 0 | 0 | 0 | 0 | 0 |
| Gas/$H_2O$ | 40 | 40 | 99 | 0 | 0 | 99 | 0 | 0 | 0 | 0 | 0 | 0 | 0 | 0 |
| Benzene | 20 | 54 | 33 | 33 | 0 | 0 | 0 | 0 | 0 | 0 | 0 | 0 | 0 | 0 |
| Toluene | 100 | 324 | 224 | 224 | 0 | 0 | 0 | 0 | 0 | 0 | 0 | 0 | 0 | 0 |
| p-X | 0 | 0 | 109 | 0 | 109 | 0 | 137 | 134 | 4 | 4 | 0 | 28 | 28 | 0 |
| m-X + o-X | 0 | 0 | 27 | 0 | 27 | 0 | 123 | 0 | 123 | 120 | 2 | 96 | 96 | 0 |
| C9 + A | 0 | 0 | 4 | 0 | 0 | 4 | 0 | 0 | 0 | 0 | 0 | 0 | 0 | 0 |
| Total | 240 | 508 | 508 | 268 | 136 | 103 | 260 | 134 | 127 | 124 | 3 | 124 | 124 | 0 |

TABLE VII (Example 7, Inventive) (PA-50)

Weight in Stream (Parts)

| Component | 301 | 303 | 305 | 306 | 307 | 308 | 309 | 310 | 311 | 313 | 315 | 317 | 319 | 321 | 322 | 323 | 324 | 325 |
|---|---|---|---|---|---|---|---|---|---|---|---|---|---|---|---|---|---|---|
| Methanol | 80 | 91 | 11 | 11 | 0 | 0 | 0 | 0 | 0 | 0 | 0 | 0 | 0 | 0 | 0 | 0 | 0 | 0 |
| Gas/$H_2O$ | 41 | 41 | 99 | 0 | 0 | 99 | 0 | 0 | 0 | 0 | 0 | 0 | 0 | 0 | 0 | 0 | 0 | 0 |
| Benzene | 0 | 0 | 0 | 0 | 0 | 0 | 0 | 0 | 0 | 49 | 20 | 29 | 0 | 0 | 0 | 0 | 29 | 0 |
| Toluene | 100 | 391 | 242 | 242 | 0 | 0 | 0 | 0 | 0 | 0 | 0 | 49 | 0 | 0 | 0 | 0 | 0 | 49 |
| p-X | 0 | 0 | 132 | 0 | 132 | 0 | 136 | 134 | 1 | 5 | 0 | 8 | 8 | 0 | 4 | 4 | 0 | 0 |
| m-X + o-X | 0 | 0 | 33 | 0 | 33 | 0 | 49 | 0 | 49 | 64 | 0 | 32 | 32 | 0 | 16 | 16 | 0 | 0 |
| C9 + A | 0 | 0 | 5 | 0 | 0 | 5 | 0 | 0 | 0 | 0 | 0 | 2 | 0 | 2 | 0 | 0 | 0 | 0 |
| Total | 220 | 522 | 522 | 253 | 164 | 105 | 184 | 134 | 50 | 119 | 20 | 119 | 40 | 2 | 20 | 20 | 29 | 49 |

TABLE VIII (Example 8, Comparative) (PA-75)

Weight in Stream (Parts)

| Component | 101 | 103 | 105 | 106 | 107 | 108 | 109 | 110 | 111 | 115 | 116 | 119 | 120 | 121 |
|---|---|---|---|---|---|---|---|---|---|---|---|---|---|---|
| Methanol | 76 | 86 | 10 | 10 | 0 | 0 | 0 | 0 | 0 | 0 | 0 | 0 | 0 | 0 |
| Gas/$H_2O$ | 39 | 39 | 95 | 0 | 0 | 95 | 0 | 0 | 0 | 0 | 0 | 0 | 0 | 0 |
| Benzene | 18 | 47 | 29 | 29 | 0 | 0 | 0 | 0 | 0 | 0 | 0 | 0 | 0 | 0 |
| Toluene | 100 | 317 | 217 | 217 | 0 | 0 | 0 | 0 | 0 | 0 | 0 | 0 | 0 | 0 |
| p-X | 0 | 0 | 107 | 0 | 107 | 0 | 134 | 131 | 4 | 4 | 0 | 28 | 28 | 0 |
| m-X + o-X | 0 | 0 | 26 | 0 | 26 | 0 | 120 | 0 | 120 | 118 | 2 | 94 | 94 | 0 |
| C9 + A | 0 | 0 | 4 | 0 | 0 | 4 | 0 | 0 | 0 | 0 | 0 | 0 | 0 | 0 |
| Total | 233 | 489 | 489 | 257 | 133 | 100 | 254 | 131 | 124 | 121 | 2 | 121 | 121 | 0 |

TABLE IX (Example 9, Inventive) (PA-75)

Weight in Stream (Parts)

| Component | 301 | 303 | 305 | 306 | 307 | 308 | 309 | 310 | 311 | 313 | 315 | 317 | 319 | 321 | 322 | 323 | 324 | 325 |
|---|---|---|---|---|---|---|---|---|---|---|---|---|---|---|---|---|---|---|
| Methanol | 77 | 88 | 11 | 11 | 0 | 0 | 0 | 0 | 0 | 0 | 0 | 0 | 0 | 0 | 0 | 0 | 0 | 0 |
| Gas/$H_2O$ | 40 | 40 | 96 | 0 | 0 | 96 | 0 | 0 | 0 | 0 | 0 | 0 | 0 | 0 | 0 | 0 | 0 | 0 |
| Benzene | 0 | 0 | 0 | 0 | 0 | 0 | 0 | 0 | 0 | 45 | 18 | 27 | 0 | 0 | 0 | 0 | 27 | 0 |
| Toluene | 100 | 379 | 235 | 235 | 0 | 0 | 0 | 0 | 0 | 0 | 0 | 44 | 0 | 0 | 0 | 0 | 0 | 44 |
| p-X | 0 | 0 | 128 | 0 | 128 | 0 | 133 | 131 | 2 | 3 | 0 | 7 | 7 | 0 | 2 | 5 | 0 | 0 |
| m-X + o-X | 0 | 0 | 32 | 0 | 32 | 0 | 53 | 0 | 53 | 61 | 0 | 29 | 29 | 0 | 7 | 22 | 0 | 0 |
| C9 + A | 0 | 0 | 5 | 0 | 0 | 5 | 0 | 0 | 0 | 0 | 0 | 2 | 0 | 2 | 0 | 0 | 0 | 0 |
| Total | 217 | 507 | 507 | 246 | 159 | 101 | 186 | 131 | 55 | 109 | 18 | 109 | 36 | 2 | 9 | 27 | 27 | 44 |

TABLE X (Example 10, Comparative) (PA-100)

Weight in Stream (Parts)

| Component | 101 | 103 | 105 | 106 | 107 | 108 | 109 | 110 | 111 | 115 | 116 | 119 | 120 | 121 |
|---|---|---|---|---|---|---|---|---|---|---|---|---|---|---|
| Methanol | 73 | 83 | 10 | 10 | 0 | 0 | 0 | 0 | 0 | 0 | 0 | 0 | 0 | 0 |
| Gas/$H_2O$ | 37 | 37 | 92 | 0 | 0 | 92 | 0 | 0 | 0 | 0 | 0 | 0 | 0 | 0 |
| Benzene | 16 | 42 | 26 | 26 | 0 | 0 | 0 | 0 | 0 | 0 | 0 | 0 | 0 | 0 |
| Toluene | 100 | 310 | 210 | 210 | 0 | 0 | 0 | 0 | 0 | 0 | 0 | 0 | 0 | 0 |
| p-X | 0 | 0 | 105 | 0 | 105 | 0 | 132 | 128 | 4 | 4 | 0 | 27 | 27 | 0 |
| m-X + o-X | 0 | 0 | 26 | 0 | 26 | 0 | 118 | 0 | 118 | 115 | 2 | 92 | 92 | 0 |
| C9 + A | 0 | 0 | 4 | 0 | 0 | 4 | 0 | 0 | 0 | 0 | 0 | 0 | 0 | 0 |
| Total | 226 | 473 | 473 | 246 | 130 | 96 | 249 | 128 | 121 | 119 | 2 | 119 | 119 | 0 |

TABLE XI (Example 11, Inventive) (PA-100)

Weight in Stream (Parts)

| Component | 301 | 303 | 305 | 306 | 307 | 308 | 309 | 310 | 311 | 313 | 315 | 317 | 319 | 321 | 322 | 323 | 324 | 325 |
|---|---|---|---|---|---|---|---|---|---|---|---|---|---|---|---|---|---|---|
| Methanol | 75 | 85 | 10 | 10 | 0 | 0 | 0 | 0 | 0 | 0 | 0 | 0 | 0 | 0 | 0 | 0 | 0 | 0 |
| Gas/$H_2O$ | 38 | 38 | 93 | 0 | 0 | 93 | 0 | 0 | 0 | 0 | 0 | 0 | 0 | 0 | 0 | 0 | 0 | 0 |
| Benzene | 0 | 0 | 0 | 0 | 0 | 0 | 0 | 0 | 0 | 40 | 16 | 24 | 0 | 0 | 0 | 0 | 24 | 0 |
| Toluene | 100 | 368 | 228 | 228 | 0 | 0 | 0 | 0 | 0 | 0 | 0 | 40 | 0 | 0 | 0 | 0 | 0 | 40 |
| p-X | 0 | 0 | 124 | 0 | 124 | 0 | 130 | 129 | 2 | 2 | 0 | 6 | 6 | 0 | 0 | 6 | 0 | 0 |

TABLE XI-continued (Example 11, Inventive) (PA-100)

| | Weight in Stream (Parts) | | | | | | | | | | | | | | | | | |
|---|---|---|---|---|---|---|---|---|---|---|---|---|---|---|---|---|---|---|
| Component | 301 | 303 | 305 | 306 | 307 | 308 | 309 | 310 | 311 | 313 | 315 | 317 | 319 | 321 | 322 | 323 | 324 | 325 |
| m-X + o-X | 0 | 0 | 31 | 0 | 31 | 0 | 58 | 0 | 58 | 58 | 0 | 27 | 27 | 0 | 0 | 27 | 0 | 0 |
| C9 + A | 0 | 0 | 5 | 0 | 0 | 5 | 0 | 0 | 0 | 0 | 0 | 2 | 0 | 2 | 0 | 0 | 0 | 0 |
| Total | 213 | 492 | 492 | 239 | 155 | 99 | 188 | 129 | 59 | 99 | 16 | 99 | 33 | 2 | 0 | 33 | 24 | 40 |

The invention claimed is:

1. A process for making para-xylene, the process comprising:
   (A) feeding a first feed comprising toluene and/or benzene to a first reactor;
   (B) conducting reactions in the first reactor to produce a first product mixture comprising toluene and mixed xylenes, and optionally benzene;
   (C) separating the first product mixture in a first separation device to obtain a first toluene-rich stream and a first xylene-rich stream;
   (D) separating the first xylene-rich stream in a second separation device to obtain a para-xylene-rich product stream, and a meta-xylene-rich stream;
   (E) feeding a third feed comprising benzene and at least a portion of the meta-xylene-rich stream to a second reactor; and
   (F) conducting transalkylation reactions in the second reactor in the presence of a transalkylation catalyst under transalkylation conditions to obtain a second reaction product mixture comprising benzene, toluene, and mixed xylenes, wherein the second reactor comprises a divided wall reactive distillation column comprising a dividing wall, a transalkylation reaction zone on one side of the dividing wall, and a distillation zone on the other side of the dividing wall; and
   wherein step (F) further comprises:
      (F-1) feeding at least a portion of the meta-xylene-rich stream to the reaction zone at a first location;
      (F-2) feeding at least a portion of the third feed to the reaction zone at a second location below the first location;
      (F-3) obtaining a lower xylene-rich stream below the second location, and recycling at least a portion of the lower xylene-rich stream to the reaction zone at a location above the second location;
      (F-4) obtaining a upper benzene-rich stream above the first location, and recycling at least a portion of the upper benzene-rich stream to the reaction zone at a location below the first location; and
      (F-5) obtaining a toluene-rich stream from the distillation zone.

2. The process of claim 1, wherein the toluene-rich stream obtained in step (F-5) comprises toluene at a concentration of at least 95 wt %, and at least a portion of the toluene-rich stream is recycled to the first reactor in step (A).

3. The process of claim 1, further comprising:
   (G) separating the second reaction product mixture in a third separation device to obtain a second toluene-rich stream and a second xylene-rich stream comprising mixed xylenes.

4. The process of claim 3, further comprising:
   (H) feeding at least a portion of the second xylene-rich stream into the second separation device in step (D).

5. The process of claim 4, wherein at least 50 wt % of the second xylene-rich stream is fed to the second separation device;
   wherein (A) further comprises feeding a second feed comprising a methylation agent to the first reactor in addition to the first feed; and
   wherein the first feed, the second feed, and the third feed, taken together, have a toluene to benzene molar ratio of at least 1.0.

6. The process of claim 3, further comprising:
   (I) feeding at least a portion of the second xylene-rich stream into the second reactor.

7. The process of claim 6, wherein at least 50 wt % the second xylene-rich stream is fed to the second reactor;
   wherein (A) further comprises feeding a second feed comprising a methylation agent to the first reactor in addition to the first feed; and
   wherein the first feed, the second feed, and the third feed, taken together, have a benzene to toluene molar ratio of at least 1.0.

8. The process of claim 6, wherein all of the second xylene-rich stream is fed into the second reactor.

9. The process of claim 3, wherein
   at least a portion of the second toluene-rich stream obtained in step (G) is recycled to the first reactor.

10. The process of claim 3, wherein:
    in step (G), a first benzene-rich stream is obtained; and
    at least a portion of the first benzene-rich stream is recycled to the second reactor.

11. The process of claim 1, wherein (A) further comprises feeding a second feed comprising a methylation agent to the first reactor in addition to the first feed; and
    wherein the first feed, the second feed, and the third feed taken together have a methyl group to benzene ring molar ratio in a range from 0.5 to 2.0.

12. The process of claim 1, wherein in step (F), the reaction mixture in the second reactor has a methyl group to benzene ring molar ratio in a range from 0.8 to 1.2.

13. The process of claim 1, wherein at least a portion of the first toluene-rich stream obtained in step (C) is recycled to the first reactor.

14. The process of claim 1, wherein at least 50% by mole of the xylenes in the second reactor is present in liquid phase, and the transalkylation reaction conditions comprise a temperature in a range from 100° C. to 500° C., and an absolute total internal pressure in a range from 100 kPa to 10,000 kPa.

15. The process of claim 1, wherein at least 90% by mole of the xylenes in the second reactor is present in vapor phase, and the transalkylation reaction conditions comprise a temperature in a range from 200° C. to 600° C., and an absolute total internal pressure in a range from 100 kPa to 10,000 kPa.

16. The process of claim 1, wherein in step (D), the second separation device comprises a SMBA type device and/or a crystallization device.

17. The process of claim 1, wherein (A) further comprises feeding a second feed comprising an alkylation agent to the first reactor in addition to the first feed;
  wherein the alkylation agent comprises methanol, dimethyl ether, or a mixture thereof; wherein in steps (A) and (B), the first reactor comprises an alkylation reactor; and wherein in step (B), toluene reacts with the alkylation agent in the presence of an alkylation catalyst under alkylation conditions.

18. The process of claim 17, wherein the alkylation conditions comprises a temperature in a range from 400° C. to 800° C., and an absolute total internal pressure from 100 kPa to 10,000 kPa.

19. The process of claim 1, wherein in steps (A) and (B), the first reactor comprises a toluene disproportionation reactor, and in step (B), toluene undergoes disproportionation reactions in the presence of a disproportionation catalyst under disproportionation conditions.

20. The process of claim 19, wherein the disproportionation conditions comprises a temperature in a range from 300° C. to 550° C., and an absolute total internal pressure from 500 kPa to 3,000 kPa.

21. The process of claim 1, wherein in step (E), a C9+A component is fed into the second reactor.

\* \* \* \* \*